Figure 1:
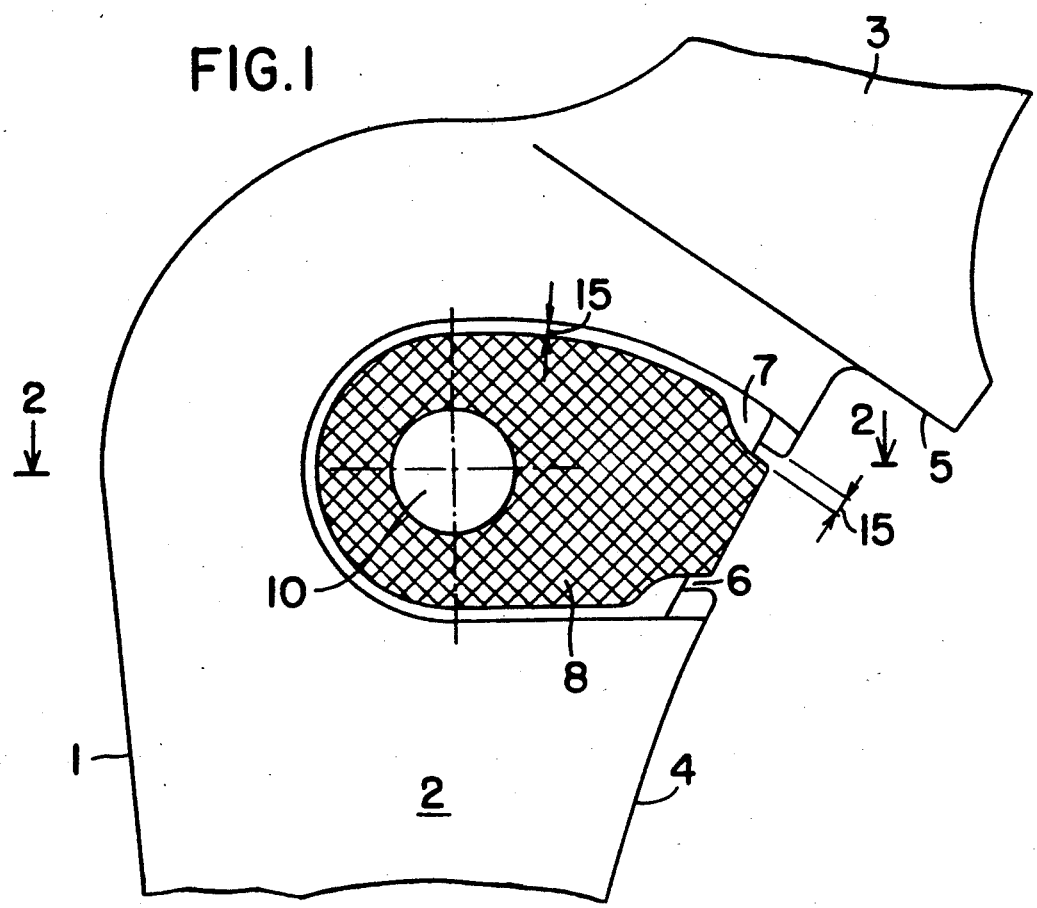

United States Patent [19]
Spotorno et al.

[11] Patent Number: 5,192,331
[45] Date of Patent: Mar. 9, 1993

[54] SHANK FOR A FEMUR HEAD PROSTHESIS

[75] Inventors: Lorenzo Spotorno, Finale Ligure, Italy; Otto Frey, Winterthur, Switzerland

[73] Assignee: Sulzer Brothers Limited, Winterthur, Switzerland

[21] Appl. No.: 784,895

[22] Filed: Oct. 30, 1991

[30] Foreign Application Priority Data

Nov. 16, 1990 [CH] Switzerland ............ 03645/90

[51] Int. Cl.$^5$ .............................................. A61F 2/36
[52] U.S. Cl. ...................................... 623/23; 623/16; 623/18
[58] Field of Search .............. 623/16, 18, 22, 23

[56] References Cited
U.S. PATENT DOCUMENTS 4,187,559 2/1980 Grell et al. ................... 623/18

FOREIGN PATENT DOCUMENTS

| | | |
|---|---|---|
| 0189546 | 8/1986 | European Pat. Off. . |
| 0234358 | 9/1987 | European Pat. Off. . |
| 0359672 | 3/1990 | European Pat. Off. . |
| 0404716 | 12/1990 | European Pat. Off. . |
| 2305961 | 10/1976 | France . |
| 2633510 | 1/1990 | France . |

*Primary Examiner*—Ronald Frinks
*Attorney, Agent, or Firm*—Kenyon & Kenyon

[57] ABSTRACT

The shank for a femur head prosthesis is provided with a cavity in the approximate region which is filled with a plastic or elastic filler. A covering is provided over the filler to avoid contact between the filler and the bone or the bone cement surrounding the shank. The covering reduces the area of contact between the bone the filler to a minimum and limits the "flow" of the filler under compressive loadings on the head of the prosthesis.

27 Claims, 1 Drawing Sheet

U.S. Patent     Mar. 9, 1993     5,192,331

SHANK FOR A FEMUR HEAD PROSTHESIS

This invention relates to a shank for a femur head prosthesis. More particularly, this invention relates to an anchoring shank for a femur head prosthesis.

As is known, various types of shanks have been provided for anchoring in a femur. For example, Swiss Patent Application 02316/89-6 describes an anchoring shank provided with a cavity between a shank and a collar with the cavity extending from a medial side of the shank and filled with an elastic member. In this construction, the neck of the prosthesis is able to flex relative to the shank body with the elastic filler providing protection against alternating loadings upon the collar of the prosthesis which rests against the bone tissue. However, in such a construction, inadequacies have appeared in practice. For example, under compressive loads, the open sides of the cavity permit the elastic filler to "bulge out" of the shank. This leads to an inadmissibly long "spring travel" of the upper part of the prosthesis with the collar relative to the shank of the prosthesis which is anchored in the bone. Secondly, the alternating loadings and unloadings of the prosthesis lead to abrasion of the filler from which particles may pass into the bone tissue. Furthermore, the material of the filler may be influenced in the course of time by contact with the living tissue or bone cement whereby, under certain circumstances, the properties of the material become disadvantageously altered.

Accordingly, it is an object of the invention to protect against damage to an elastic filler disposed within a cavity of a shank for a femur head prosthesis.

It is another object of the invention to avoid abrasion of any elastic filler disposed within a shank of a femur head prosthesis.

Briefly, the invention provides a shank for a femur head prosthesis which is comprised of a body for implanting in a femur, a neck which extends from one end of the body, and a collar which is disposed between a body and the neck with the collar having a base for bearing on cortical tissue of a femur and a cavity in the shank. In this respect, the cavity extends from a medial side of the shank towards a lateral side of the shank with an opening in the medial side. In addition, the shank is provided with an elastic filler in the cavity for damping movements of the neck relative to the shank.

In accordance with the invention, a covering is disposed over the filler in order to maintain the filler in the cavity during compression of the filler in response to bending of the neck relative to the body of the shank.

By use of the covering, the "possibility of flow" of the elastic filler which may be made of a plastic is, on the one hand, reduced so that the movement of the head or neck of the prosthesis with respect to the shank is limited. The damping which arises in the case of this limitation being greater the longer the travel. On the other hand, the covering has the effect that there is practically no direct contact of the filler with the bone or a bed of bone cement.

Figure 2:
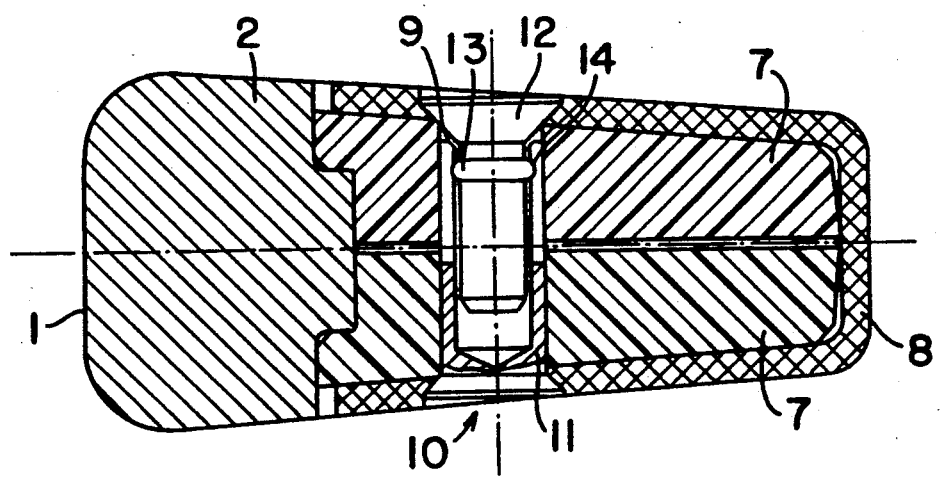

These and other objects and advantages of the invention will become more apparent from the following detailed description taken in conjunction with the accompanying drawings wherein:

FIG. 1 illustrates a side view of a proximal part of a shank for femur head prosthesis as constructed in accordance with the invention; and FIG. 2 illustrates a view taken on line II—II of FIG. 1.

Referring to FIG. 1, the shank is of generally known construction for a femur head prosthesis and includes a one piece body 2 for implanting in a femur, a neck 3 which extends from one end of the body 2 and a collar 5 which is disposed between the body 2 and the neck 3. This collar 5 also has a base for bearing on cortical tissue of a femur.

The shank body 2 consists of metal, for example, a titanium alloy, and widens conically from the distal end. A narrow lateral face 1 continues proximally first of all via a circular arc into the horizontal direction, as viewed, and then into the neck 3 of the prosthesis. The neck 3, in turn, carries a conical stud (not shown) to which a joint-head (not shown) may be attached.

The shank body 2 has a medial narrow face 4 which runs along a steady curve and ends in the collar 5. The base of the collar 5 which forms a bearing area to bear against the cortical tissue of the bone of the femur (not shown) may be provided with a structure which promotes growth of the bone.

A few millimeters below the collar 5, the shank body 2 has a balloon-like cavity 6 which extends from the opening in the narrow medial side 4 towards the lateral side. This cavity is filled with a highly elastic filler 7 which, in the present example, consists of polyurethane or polyethylene, and which serves to damp movements of the neck 3 relative to the shank body 2.

For reasons of assembly, the filler 7 as shown in FIG. 2 is in two parts and defines anterior, posterior and medial sides which are surrounded by a U-shaped covering 8 of metal which, in the example shown, consists of a multilayer wire netting or mesh into the meshes of which bone can grow or bone cement can penetrate. The covering 8 may also be formed of sheetmetal which furthermore may likewise be covered with a wire mesh or netting promoting contact with the bone.

The covering 8 is recessed into the contour of the shank body 2. In order to enable relative movements between the head and neck 3 of the prosthesis, on the one hand, and the shank body 2 on the other, a clearance 15 is provided along the whole periphery of the covering 8 between the covering 8 and the boundary of the cavity 6 in the shank body 2.

The covering 8 is disposed over the filler 7 in order to maintain the filler 7 in the cavity 6 in response to bending of the neck 3 relative to the shank body 2.

Referring to FIG. 2, the U-shaped covering 8 has a pair of legs for holding the filler 7 therebetween. In addition, the legs and the filler 7 are provided with aligned holes which extend in a ventral/dorsal direction for receiving a closure 10 for holding the covering 8 and filler 7 together. In the example shown, the closure 10 includes a sleeve 11 having a head at one end which extends through one of the legs into the filler 7 as well as a stud 12 which likewise has a head at one end and which extends through the other leg of the covering 8 into engagement with the sleeve 11. The sleeve 11 also has an internal groove or groove-like depression 14 while the stud 12 has an external bead 13 for snapping into the groove 14.

The invention thus provides a relatively simple structure to prevent bulging out of the elastic filler in a shank of a femur head prosthesis under compressive loads. Further, the invention provides a relatively simple construction to prevent contact between the material of the filler and living tissue or bone cement which may be otherwise deleterious to the material of the filler.

What is claimed is:

1. A shank for a femur head prosthesis comprising
a body for implanting in a femur;
a neck extending from one end of said body;
a collar disposed between said body and said neck, said collar having a base for bearing on cortical tissue of a femur;
a cavity in said shank, said cavity extending from a medial side of said shank towards a lateral side of said shank with an opening in said medial side;
an elastic filler in said cavity for damping movements of said neck relative to said shank body; and
a covering disposed over said filler to maintain said filler in said cavity during compression of said filler in response to bending of said neck relative to said body wherein said covering is of U shape and is inserted into said cavity from said medial side.

2. A shank as set forth in claim 1 wherein said covering is disposed in said cavity within the contour of said body with a clearance between said covering and said body.

3. A shank as set forth in claim 2 wherein said covering is made of metal mesh to promote an ingrowth of tissue.

4. A shank as set forth in claim 1 wherein said covering is made of metal mesh to promote an ingrowth of tissue.

5. A shank as set forth in claim 1 wherein said covering includes an inner layer of sheet metal and an outer layer of metal mesh.

6. A shank as set forth in claim 1 wherein said covering is of U shape with a pair of legs holding said filler therebetween.

7. A shank as set forth in claim 6 wherein said filler and each leg has a hole extending in a ventral/dorsal direction, and which further comprises a closure in said holes for holding said covering and said filler together.

8. A shank as set forth in claim 7 wherein said closure includes a sleeve having a head at one end and extending through one of said legs into said filler and a stud having a head at one end and extending through the other of said legs into engagement within said sleeve.

9. A shank is set forth in claim 8 wherein said sleeve has an internal groove and said stud has an external bead for snapping into said groove.

10. A shank for a femur head prosthesis comprising
a body for implanting in a femur;
a neck extending from one end of said body;
a collar disposed between said body and said neck, said collar having a base for bearing on cortical tissue of a femur;
a cavity in said shank, said cavity extending from a medial side of said shank towards a lateral side of said shank with an opening in said medial side;
an elastic filler in said cavity for damping movements of said neck relative to said shank body; and
a covering disposed over said filler to maintain said filler in said cavity during compression of said filler in response to bending of said neck relative to said body, wherein said covering is disposed in said cavity within the contour of said body with a clearance between said covering and said body, and wherein said covering is made of metal mesh to promote an ingrowth of tissue.

11. A shank for a femur head prosthesis comprising
a body for implanting in a femur;
a neck extending from one end of said body;
a collar disposed between said body and said neck, said collar having a base for bearing on cortical tissue of a femur;
a cavity in said shank, said cavity extending from a media side of said shank towards a lateral side of said shank with an opening in said medial side;
an elastic filler in said cavity for damping movements of said neck relative to said shank body; and
a covering disposed over said filler to maintain said filler in said cavity during compression of said filler in response to bending of said neck relative to said body, wherein said covering is made of metal mesh to promote an ingrowth of tissue.

12. A shank for a femur head prosthesis comprising
a body for implanting in a femur;
a neck extending from one end of said body;
a collar disposed between said body and said neck, said collar having a base for bearing on cortical tissue of a femur;
a cavity in said shank, said cavity extending from a medial side of said shank towards a lateral side of said shank with an opening in said medial side;
an elastic filler in said cavity for damping movements of said neck relative to said shank body; and
a covering disposed over said filler to maintain said filler in said cavity during compression of said filler in response to bending of said neck relative to said body, wherein said covering includes an inner layer of sheet metal and an outer layer of metal mesh.

13. A shank for a femur head prosthesis comprising
a body for implanting in a femur;
a neck extending from one end of said body;
a collar disposed between said body and said neck, said collar having a base for bearing on cortical tissue of a femur;
a cavity in said shank, said cavity extending from a medial side of said shank towards a lateral side of said shank with an opening in said medial side;
an elastic filler in said cavity for damping movements of said neck relative to said shank body; and
a covering disposed over said filler to maintain said filler in said cavity during compression of said filler in response to bending of said neck relative to said body, wherein said covering is of U shape with a pair of legs holding said filler therebetween.

14. A shank as set forth in claim 13 wherein said filler and each leg has a hole extending in a ventral/dorsal direction, and which further comprises a closure in said holes for holding said covering and said filler together.

15. A shank as set forth in claim 14 wherein said closure includes a sleeve having a head at one end and extending through one of said legs into said filler and a stud having a head at one end and extending through the other of said legs into engagement within said sleeve.

16. A shank as set forth in claim 15 wherein said sleeve has an internal groove and said stud has an external bead for snapping into said groove.

17. A shank for a femur head prosthesis comprising
a single piece body for implanting in a femur;
a neck extending from one end of said body;
a collar disposed between said body and said neck, said collar having a base for bearing on cortical tissue of a femur;

a cavity in said shank, said cavity extending from a medial side of said shank towards a lateral side of said shank with an opening in said medial side;

an elastic filler in said cavity for damping movements of said neck relative to said shank body; and a sheet covering disposed over said filler to maintain said filler in said cavity during compression of said filler in response to bending of said neck relative to said body.

18. A shank as set forth in claim 17 wherein said filler includes anterior, posterior, and medial sides and wherein said sheet covering is disposed over said filler from said anterior and posterior sides to said medial side of said filler.

19. A shank as set forth in claim 17 wherein said sheet covering is disposed in said cavity within the contour of said body with a clearance between said sheet covering and said body.

20. A shank as set forth in claim 19 wherein said sheet covering is made of metal mesh to promote an ingrowth of tissue.

21. A shank as set forth in claim 17 wherein said sheet covering is made of metal mesh to promote an ingrowth of tissue.

22. A shank as set forth in claim 17 wherein said sheet covering includes an inner layer of sheet metal and an outer layer of metal mesh.

23. A shank as set forth in claim 17 wherein said sheet covering is of U shape and is inserted into said cavity from said medial side.

24. A shank as set forth in claim 17 wherein said sheet covering is of U shape with a pair of legs holding said filler therebetween.

25. A shank as set forth in claim 24 wherein said filler and each leg has a hole extending in a ventral/dorsal direction, and which further comprises a closure in said holes for holding said sheet covering and said filler together.

26. A shank as set forth in claim 25 wherein said closure includes a sleeve having a head at one end and extending through one of said legs into said filler and a stud having a head at one end and extending through the other of said legs into engagement within said sleeve.

27. A shank as set forth in claim 26 wherein said sleeve has an internal groove and said stud has an external bead for snapping into said groove.

* * * * *